US010092661B2

(12) United States Patent
Qian et al.

(10) Patent No.: US 10,092,661 B2
(45) Date of Patent: *Oct. 9, 2018

(54) STABLE COLLOIDAL GOLD NANOPARTICLES WITH CONTROLLABLE SURFACE MODIFICATION AND FUNCTIONALIZATION

(71) Applicant: IMRA America, Inc., Ann Arbor, MI (US)

(72) Inventors: Wei Qian, Ann Arbor, MI (US); Makoto Murakami, Ann Arbor, MI (US); Yuki Ichikawa, Kariya Aichi (JP); Yong Che, Ann Arbor, MI (US)

(73) Assignee: IMRA America, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,416

(22) Filed: Feb. 24, 2014

(65) Prior Publication Data

US 2014/0170070 A1 Jun. 19, 2014

Related U.S. Application Data

(62) Division of application No. 13/038,788, filed on Mar. 2, 2011, now Pat. No. 8,697,129.

(51) Int. Cl.

| | |
|---|---|
| *A61K 49/00* | (2006.01) |
| *G01N 21/64* | (2006.01) |
| *G01N 33/531* | (2006.01) |
| *G01N 33/543* | (2006.01) |
| *A61K 9/00* | (2006.01) |
| *A61K 9/16* | (2006.01) |
| *B01J 13/00* | (2006.01) |
| *A61K 41/00* | (2006.01) |
| *A61K 47/10* | (2017.01) |
| *G01N 21/65* | (2006.01) |
| *B82Y 5/00* | (2011.01) |
| *B82Y 40/00* | (2011.01) |
| *G01N 21/35* | (2014.01) |
| *B82Y 30/00* | (2011.01) |

(52) U.S. Cl.

CPC ........ *A61K 49/0002* (2013.01); *A61K 9/0019* (2013.01); *A61K 9/1688* (2013.01); *A61K 41/0057* (2013.01); *A61K 47/10* (2013.01); *B01J 13/0034* (2013.01); *B01J 13/0043* (2013.01); *G01N 21/64* (2013.01); *G01N 21/658* (2013.01); *G01N 33/531* (2013.01); *G01N 33/54346* (2013.01); *B82Y 5/00* (2013.01); *B82Y 30/00* (2013.01); *B82Y 40/00* (2013.01); *G01N 2021/3595* (2013.01)

(58) Field of Classification Search
CPC combination set(s) only.
See application file for complete search history.

(56) References Cited

U.S. PATENT DOCUMENTS

| | | | |
|---|---|---|---|
| 9,234,078 B2 | 1/2016 | Sun et al. | |
| 9,587,071 B2 | 3/2017 | Sun et al. | |
| 2009/0169807 A1 | 7/2009 | Yang et al. | |
| 2010/0028559 A1 | 2/2010 | Yan et al. | |
| 2010/0276638 A1* | 11/2010 | Liu et al. | 252/301.35 |
| 2011/0165647 A1 | 7/2011 | Fernig et al. | |
| 2013/0052130 A1 | 2/2013 | Davis et al. | |

FOREIGN PATENT DOCUMENTS

| | | |
|---|---|---|
| CN | 1554503 A | 12/2003 |
| JP | H1073594 A | 3/1998 |
| JP | 2005534925 A | 11/2005 |
| JP | 2008297614 A | 12/2008 |
| JP | 2009299112 A | 12/2009 |
| JP | 2014515009 A | 6/2014 |
| WO | 2010007117 | 1/2010 |

OTHER PUBLICATIONS

Mei et al., Langmuir 2009, 25(19), 10604-10611.*
Amendola et al., J. Mater. Chem., 2007, 17, 4705-4710.*
Haes et al., "Solution-Phase, Triangular Ag Nanotriangle Fabricated by Nanosphere Lithography," Journal of Physical Chemistry B, vol. 109 (2005), 11158.
Hill et al., "The Role Radius of Curvature Plays in Thiolated Oligonucleotide Loading on Gold Nanoparticles," ACS Nano, vol. 3 (2009), 418-424.

(Continued)

*Primary Examiner* — Robert S Cabral
(74) *Attorney, Agent, or Firm* — Dickinson Wright, PLLC

(57) ABSTRACT

In the present invention, a method of producing stable bare colloidal gold nanoparticles is disclosed. The nanoparticles can subsequently be subjected to partial or full surface modification. The method comprises preparation of colloidal gold nanoparticles in a liquid by employing a top-down nanofabrication method using bulk gold as a source material. The surface modification of these nanoparticles is carried out by adding one or multiple types of ligands each containing functional groups which exhibit affinity for gold nanoparticle surfaces to produce the conjugates. Because of the high efficiency and excellent stability of the nanoparticles produced by this method, the fabricated gold nanoparticle conjugates can have surface coverage with functional ligands which can be tuned to be any percent value between 0 and 100%.

27 Claims, 9 Drawing Sheets

(56) References Cited

OTHER PUBLICATIONS

Liao et al., "Gold Nanorod Bioconjugates," Chem. Mater., vol. 17 (2005), 4636-4641.
Ojea-Jimenez et al.,"Instability of Cationic Gold Nanoparticle Bioconjugates: The Role of Citrate Ions," J. Am. Chem. Soc., vol. 131 (2009), 13320-13327.
C. Tabor et al., "Dependence of the Threshold Energy of Femtosecond Laser Ejection of Gold Nanoprisms from Quartz Substrates on the Nanoparticle Environment," J. of Physical Chemistry C, vol. 111 (2007), 8934-8941.
G. H. Woehrle et al., "Thiol-Functionalized, 1.5-nm Gold Nanoparticles Through Ligand Exchange Reactions: Scope and Mechanism of Ligand Exchange," J. Am. Chem. Soc., vol. 127 (2005), 2172-2183.
A.V. Simaken et al., "Nanodisks of Au and Ag produced by laser ablation in liquid environment", Chemical Physics Letters vol. 348, 2001, pp. 182-186.
State Intellectual Property Office of the People's Republic of China, English Translation of First Office Action, dated May 14, 2015, 14 Pages.
PCT International Search Report and Written Opinion issued in International Application No. PCT/US2012/027213.

\* cited by examiner

STABLE COLLOIDAL GOLD NANOPARTICLES WITH CONTROLLABLE SURFACE MODIFICATION AND FUNCTIONALIZATION

RELATED APPLICATIONS

This is a divisional application of application Ser. No. 13/038,788, filed on Mar. 2, 2011.

TECHNICAL FIELD

The present invention relates to a method for the top-down fabrication of stable colloidal gold nanoparticles and the surface modification and/or functionalization of the stable colloidal gold nanoparticles produced by the method.

BACKGROUND

Colloidal gold is a dispersion of gold nanoparticles in a dispersion medium, typically water but other medium can also be used as discussed below. Gold nanoparticles have attracted substantial interest from scientists for over a century because of their unique physical, chemical, and surface properties, such as: (i) size- and shape-dependent strong optical extinction and scattering which is tunable from ultraviolate (UV) wavelengths all the way to near infrared (NIR) wavelengths; (ii) large surface areas for conjugation to functional ligands; and (iii) little or no long-term toxicity or other adverse effects in vivo allowing their high acceptance level in living systems. Colloidal gold nanoparticles, also referred to in the present specification and claims as gold nanocolloids, are now being widely investigated for its potential use in a wide variety of biological and medical applications. Applications include use as an imaging agent, a sensing agent, a gene-regulating agent, a targeted drug delivery carrier, and in photoresponsive therapeutics. Most of these applications require the colloidal gold undergo surface modification, also referred to as surface functionalization in the specification and claims of the present invention, prior to its use in the application.

Currently, the overwhelming majority of gold nanocolloids are prepared by using the standard wet chemical sodium citrate reduction of tetrachloroaurate ($HAuCl_4$) methodology. This method results in the synthesis of spherical gold nanoparticles with diameters ranging from 5 to 200 nm which are capped or covered with negatively charged citrate ions. The citrate ion capping prevents the nanoparticles from aggregating by providing electrostatic repulsion. Once formed and prior to their use in biological and medical applications the sodium citrate capped gold nanoparticles must undergo further surface functionalization, usually via conjugation of functional ligand molecules to the surface of the nanoparticle.

Other wet chemical methods for formation of colloidal gold include the Brust method, the Perrault method and the Martin method. The Brust method relies on reaction of chlorauric acid with tetraoctylammonium bromide in toluene and sodium borohydride. The Perrault method uses hydroquinone to reduce the $HAuCl_4$ in a solution containing gold nanoparticle seeds. The Martin method uses reduction of $HAuCl_4$ in water by $NaBH_4$ wherein the stabilizing agents HCl and NaOH are present in a precise ratio. All of the wet chemical methods rely on first converting gold (Au) with strong acid into the atomic formula $HAuCl_4$ and then using this atomic form to build up the nanoparticles in a bottom-up type of process. All of the methods require the presence of stabilizing agents to prevent the gold nanoparticles from aggregating and precipitating out of solution. Once the stabilized nanoparticles are formed further surface functionalization must occur before the nanoparticles can be used in their many potential applications. These surface modifications also must not result in destabilization of the colloidal suspension and precipitation of the gold nanoparticles. Ligand exchange reactions have been found to be a particularly powerful approach for surface modification of various inorganic colloidal nanoparticles including gold nanocolloids and they are widely used to produce organic and water-soluble nanoparticles with various core materials and functional groups.

One of the most difficult aspects of carrying out ligand exchange reactions involving colloidal gold nanoparticles is maintaining the stability of the colloidal suspension of gold during the reaction. As reflected in a large number of reported protocols, Woehrle, G. H., Brown, L. O., and Hutchison, J. E., *J. Am. Chem. Soc.*, Vol. 127 (2005), 2172-2183; Liao, H., and Hafner J. H., *Chem. Mater.*, Vol. 17 (2005), 4636-4641; Ojea-Jimenez, I. and Puntes, V., *J. Am. Chem. Soc.*, Vol. 131 (2009), 13320-13327, to ensure completion of the ligand exchange reaction and to avoid precipitation of gold nanoparticles it is often necessary to use a very large excess, sometimes over a 10 fold excess, of the ligand over the amount required to form a monolayer, as found by referring to the literature values for the ligand footprint on gold surfaces, on the surface of the nanoparticles. It is undesirable to have the excess unreacted free ligand left in the gold nanocolloids since it might interfere with or alter the expected functionalities of the gold nanoparticle conjugates formed. It is not easy, however, to remove the excess free ligand without inducing aggregation or leading to a noticeable loss of gold nanoparticle conjugates. It is also very difficult to create gold nanoparticles with more than one type of ligand bound to them when starting from wet chemical produced colloidal gold. Because the ligands must be added in such a large excess, generally a 1000% excess over the amount required to form a monolayer based on footprint analysis, it is not possible with current colloidal gold systems to prepare gold nanoparticles either with a defined number of ligands per nanoparticle, which would be very beneficial for many applications and fundamental studies, or with multiple ligands. Finally, because of the low conjugation efficiency, the ligand exchange reaction is not a good method for the conjugation of precious biomolecules, such as aptamers or vectors, onto gold nanoparticles.

In the present invention, we provide a top-down fabrication method to address the issues described above. In the present specification and claims a top-down fabrication method means a method which begins with a bulk material, not an atomic form of gold as in wet chemical methods, in a liquid and fabricates a stable colloidal nanoparticle suspension in the liquid. In a preferred top-down method of the present invention the method starts with a bulk gold material in a liquid and produces pure, bare, stable gold nanoparticles in a colloidal gold suspension. The produced nanoparticles are bare because the method does not require any stabilizers nor does it involve any citrate reduction. The produced gold nanoparticles can undergo surface modification and the amount of surface coverage by modifying ligands can be tuned to be any percent value between 0 and 100%. The method also allows us to fabricate gold nanoparticles conjugated with multiple types of ligands with different functions, for example, sensing, imaging, improving solubility, and preventing non-specific binding. The method does not require a large excess amount of ligand to prevent aggregation of the gold nanoparticles, thus it is adaptable to use with ligands that are in short supply or very expensive. Because the nanoparticles are bare the conjugation reaction does not involve any competition with or displacement of stabilizers such as citrate as in prior art methods. Thus, even ligands with low affinity for the gold nanoparticles can be used in the conjugation reaction.

SUMMARY OF THE INVENTION

The present invention relates to a method for producing stable bare gold nanocolloids having a size in at least one dimension of from 1 to 200 nanometers, which can be subjected to partial or full surface modification with one or more ligands for use in biological, medical, and other applications.

In one aspect, the present invention is directed to a stable chemical or biochemical reagent comprising gold nanoparticles conjugated with at least one ligand in a controllable surface coverage.

In another aspect, the present invention is directed to a stable chemical or biochemical reagent comprising gold nanoparticles conjugated with two or more different ligands.

In a further aspect, the present invention also provides a method to characterize the surface chemistry of colloidal gold nanoparticles by using changes in absorbance during conjugation of thiolated-polyethyleneglycol (PEG) to the nanoparticles.

DETAILED DESCRIPTION

Figure 1:
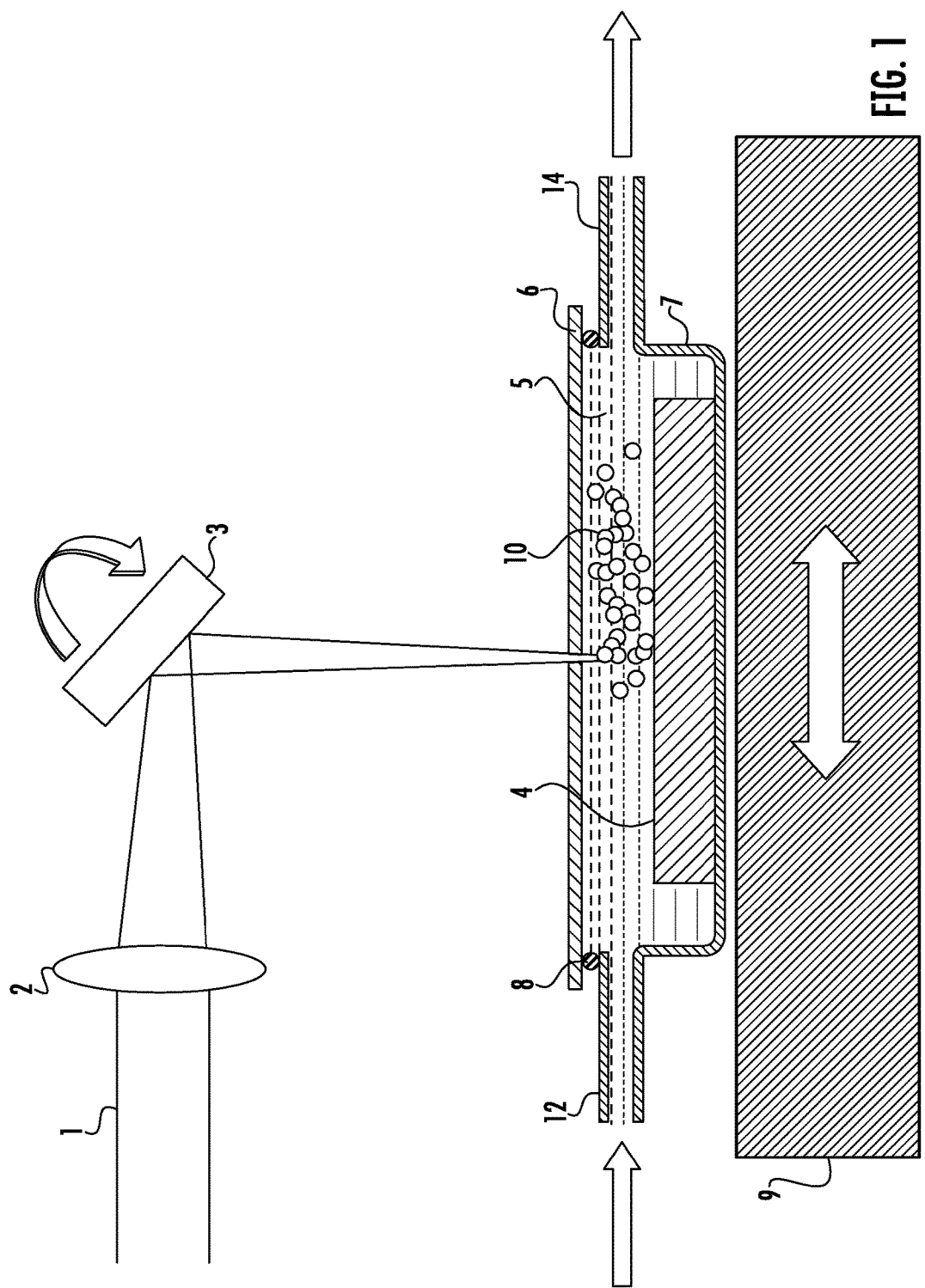
FIG. 1 schematically illustrates a laser-based ablation system for the top-down production of gold nanoparticles in a liquid in accordance with the present invention.

Gold nanocolloids have attracted strong interest from scientists for over a century and are now being heavily investigated for their potential use in a wide variety of medical and biological applications. For example, potential uses include surface-enhanced spectroscopy, biological labeling and detection, gene-regulation, and diagnostic or therapeutic agents for treatment of cancer in humans. Their versatility in a broad range of applications stems from their unique physical, chemical, and surface properties, such as: (i) size- and shape-dependent strong optical extinction and scattering at visible and near infrared (NIR) wavelengths due to a localized surface plasmon resonance of their free electrons upon excitation by an electromagnetic field; (ii) large surface areas for conjugation to functional ligands; and (iii) little or no long-term toxicity or other adverse effects in vivo allowing their high acceptance level in living systems.

These new physical, chemical, and surface properties, which are not available from either atomic or bulk counterparts, explain why gold nanocolloids have not been simply chosen as alternatives to molecule-based systems but as novel structures which provide substantive advantages in biological and medical applications.

As discussed above, the overwhelming majority of gold nanocolloids are prepared by the standard sodium citrate reduction reaction. This method allows for the synthesis of spherical gold nanoparticles with diameters ranging from 5 to 200 nanometers (nm) which are capped with negatively charged citrate ions. The capping controls the growth of the nanoparticles in terms of rate, final size, geometric shape and stabilizes the nanoparticles against aggregation by electrostatic repulsion.

While such wet chemical prepared gold nanocolloids may be stable for years in the as-synthesized solution, they immediately aggregate irreversibly in the presence of salts. In the presence of elevated salt concentrations, the electrostatic repulsion from the citrate is shielded and the gold nanoparticles can easily come close enough to each other to be within the range of the van der Waals force which causes the nanoparticles to agglomerate. Thus, as-synthesized citrate-capped gold nanocolloids are not stable in harsh biological environments such as in the presence of strong acids, strong bases, or concentrated salts and therefore they are not suitable for the applications mentioned above in the areas of biology and medicine.

The prerequisite for most of their intended biological and medical applications is the further surface modification of the as-synthesized citrate-capped gold nanoparticles via conjugation of functional ligand molecules to the surface of the gold nanoparticles. The surface functionalization of gold nanoparticles for any biological or medical applications is crucial for at least two reasons. First is control over the interaction of the nanoparticles with their environment, which is naturally taking place at the nanoparticle surface. Appropriate surface functionalization is a key step to providing stability, solubility, and retention of physical and chemical properties of the nanoparticles in the physiological conditions. Second, the ligand molecules provide additional and new properties or functionality to those found inherently in the core gold nanoparticle. These conjugated gold nanoparticles bring together the unique properties and functionality of both the core material and the ligand shell for achieving the goals of highly specific targeting of gold nanoparticles to the sites of interest, ultra-sensitive sensing, and effective therapy.

Nowadays, major strategies for surface modification of inorganic colloidal nanoparticles include ligand exchange, ligand modification, and additional coating. Among these strategies the ligand exchange reaction has proven to be a particularly powerful approach to incorporate functionality onto nanoparticles and is widely used to produce organic- and water-soluble nanoparticles with various core materials and functional groups. In the ligand exchange reaction, the original ligand molecules on the surfaces of nanoparticles are exchanged with other ligands to provide new properties or functionality to the nanoparticles. In the most cases, the incoming ligand molecule binds more strongly to the nanoparticle surface than the leaving ligand, which allows colloidal stability of the nanoparticles to be maintained during the reaction. While this is, in principle, well understood and described by theory, the full scope, exact processes, and the microscopic nature of the ligand exchange reactions involving nanoparticles have not been determined and are still subject to research and discussion. These reactions are complex because the nanoparticles, conjugating ligands, additives, residues from the nanoparticle synthesis, and the nature of the solvent all play important roles in the ligand exchange reaction.

Factors that affect surface functionalization of gold nanocolloids produced by wet chemical methods via ligand exchange reactions have been extensively investigated with the objective of optimizing such processes. Various chemical functional groups, such as thiol, amine, and phosphine, possess a high affinity for the surface of gold nanoparticles. Thiol groups are considered to show the highest affinity for gold surfaces, approximately 200 kJ/mol, and therefore a majority of gold nanoparticle surface functionalization occurs through using ligand molecules having thiol groups which bind to surfaces of gold nanoparticles via a thiol-Au bond.

In contrast to the prior process of bottom-up fabrication using wet chemical processes, the present invention produces gold nanocolloids by a top-down nanofabrication approach. The top-down fabrication methods of the present invention start with a bulk material in a liquid and then break the bulk material into nanoparticles in the liquid by applying physical energy to the material. The physical energy can be mechanical force, heat, electric field energy via arc discharge, magnetic field energy, ion beam energy, electron beam energy, or laser ablation of the bulk material. The present process produces a pure, bare and stable colloidal gold that avoids the wet chemical issues of residual chemical precursors, stabilizing agents and reducing agents.

The present invention allows for production of stable gold nanocolloids with only partial surface modification to be fabricated, where the conjugate ligand molecules are directly bound to the surfaces of gold nanoparticles via functional groups possessing certain affinity to gold surface. In addition, the present invention allows for stable gold nanoparticle conjugates with one or multiple different functional ligands directly bound to their surfaces to be fabricated. Also, the surface coverage amount of functional ligands on the surfaces of the fabricated gold nanoparticle conjugates can be tuned to be any percent value between 0 and 100%. All of these unique properties are available because the present invention produces bare gold nanoparticles that are stable in the liquid they are created in with no need for stabilizing agents.

Among the molecules used for surface functionalization of gold nanoparticles, polyethyleneglycol (PEG), or more specifically thiolated polyethyleneglycol (SH-PEG), is one of the more important and widely used species. As discussed elsewhere in the present specification many other ligands can be used to functionalize the present colloidal gold preparations including aptamers, generally through binding at a thiol functionality linked to the aptamer.

PEG is a linear polymer consisting of repeated units of —$CH_2$—$CH_2$—O—. Depending on the molecular weight, the same molecular structure is also termed poly (ethylene oxide) or polyoxyethylene. The polymer is very soluble in a number of organic solvents as well as in water. After being conjugated onto the surfaces of gold nanoparticles, in order to maximize entropy, the PEG chains have a high tendency to fold into coils or bend into a mushroom like configuration with diameters much larger than proteins of the corresponding molecular weight. The surface modification of gold nanoparticles with PEG is often referred to as 'PEGylation' and in the present specification and claims binding of PEG to gold nanoparticles will be referred to as PEGylation. Since the layer of PEG on the surface of gold nanoparticles can help to stabilize the gold nanoparticles in an aqueous environment by providing a stearic barrier between interacting gold nanoparticles, PEGylated gold nanoparticles are much more stable at high salt concentrations.

In addition, the ethylene glycol functional group in the PEG is known to interact well with water molecules and so when the PEG molecules are conjugated onto the surface of the gold nanoparticles, the spaces between the PEG chains can attract water molecules to create a hydrophilic layer of water molecules around the gold nanoparticles. This results in inert hydrophilic surface with less 'stickyness', which prevents PEGylated gold nanoparticles from being recognized and eliminated by the human reticuloendothelial system (RES) from the systemic blood circulation before reaching their targeted sites of interest through passive targeting based on the enhanced permeation and retention mechanism or active targeting with the aid of a targeting moiety and performing their intended functions. The PEG chains also provide reactive sites for adding other targeting or signaling functionality to PEGylated gold nanoparticles prepared according to the present invention. These reactive sites can be used to bind fluorescent markers for detection and signaling functions.

Since PEGylation is currently a very effective means to enhance stability and solubility of gold nanoparticles, prolong circulation time, minimize non-specific binding, and improve specific targeting to the sites of interest, conjugation of gold nanoparticles prepared according to the present invention to SH-PEG is disclosed below as one example of surface modification of these gold nanoparticles. However, the discussed strategies and results of conjugation of the present inventive gold nanoparticles to SH-PEG are of general nature and apply in the same way to binding of other ligand molecules containing at least one functional group which exhibits affinity for gold surfaces to these nanoparticles.

A first step in the present invention is the finding that stable colloidal suspensions of bare gold nanoparticles can be created by a top-down fabrication method in situ in a suspension medium in the absence of stabilizing agents. Colloidal gold nanoparticles exhibit an absorbance peak in the wavelength range of 518 to 530 nanometers (nm). The term "stable" as applied to a colloidal gold preparation prepared according to the present invention means that the absorbance intensity caused by localized surface plasmon resonance of a bare colloidal gold preparation upon storage does not vary by more than plus or minus 10% of the value as measured immediately after preparation of the bare colloidal gold preparation, obviously at the same concentration. Generally, if a colloidal gold preparation becomes unstable the gold nanoparticles begin to aggregate and precipitate out of the suspension over time, thus leading to a decrease in the absorbance at 518-530 nm. In addition, "stable" means that there is a minimal red shift or change in localized surface plasmon resonance of 2 nanometers or less. The term "bare" as applied to the colloidal gold nanoparticles prepared according to the present invention means that the nanoparticles are pure gold with no surface modification or treatment other than creation as described in the liquid. The bare gold nanoparticles are also not in the presence of any stabilizing agents, they are simply in the preparation liquid which does not contain any nanoparticle stabilizers such as citrate. The present method preferably comprises formation of bare nanoparticles; however, this does not exclude the use of stabilizers such as citrate if desired. One of the unique aspects of the present invention is that the presence of such stabilizers, while tolerated, is not required. All previous methods require use of stabilizers and surfactants and the problems associated with this requirement are discussed throughout the present specification. It is necessary that the preparation occur in a liquid so that the colloidal suspension forms as the nanoparticles are created. It is not possible to create colloidal gold by first creating dry powdered gold nanoparticles and then adding them to a suspension medium and expect to generate colloidal gold. A dry gold nanoparticle powder will not disperse in a suspension medium without the addition of one or more surfactants or other stabilizing agents such as are used in wet chemical formation methods described above. Only by following the process of the present invention can stable bare gold nanoparticle colloids be prepared in situ. There are a variety of top-down nanofabrication approaches that can be used in the present invention. All, however, require that the generation of the nanoparticles from the bulk material occur in the presence of the suspension medium. In one embodiment the process comprises a one step process wherein the application of the physical energy source, such as mechanical energy, heat, electric field energy i.e. arc discharge, magnetic field energy, ion beam energy, electron beam energy, or laser energy to the bulk gold occur in the suspension medium. The bulk source is place in the suspension medium and the physical energy applied thus the generated nanoparticles are immediately suspended in the suspension medium as they are formed. In another embodiment the present invention is a two-step process including the steps of: 1) fabricating gold nanoparticle arrays on a substrate by using photo, electron beam, focused ion beam, nanoimprint, or nanosphere lithography as known in the art; and 2) removing the gold nanoparticle arrays from the substrate into the suspension liquid using one of the physical energy methods. Tabor, C., Qian, W., and ElSayed, M. A., Journal of Physical Chemistry C, Vol 111 (2007), 8934-8941; Haes, A. J.; Zhao, J.; Zou, S. L.; Own, C. S.; Marks, L. D.; Schatz, G. C.; Van Duyne, R. P. Journal Of Physical Chemistry B, Vol 109 (2005), 11158. In both methods the colloidal gold is formed in situ by generating the nanoparticles in the suspension medium using one of the physical energy methods.

In at least one embodiment of the present invention, gold nanocolloids were produced by pulsed laser ablation of a bulk gold target in deionized water as the suspension medium. FIG. 1 schematically illustrates a laser-based system for producing colloidal suspensions of nanoparticles of complex compounds such as gold in a liquid using pulsed laser ablation in accordance with the present invention. In one embodiment a laser beam 1 is generated from an ultrafast pulsed laser source, not shown, and focused by a lens 2. The source of the laser beam 1 can be a pulsed laser or any other laser source providing suitable pulse duration, repetition rate, and/or power level as discussed below. The focused laser beam 1 then passes from the lens 2 to a guide mechanism 3 for directing the laser beam 1. Alternatively, the lens 2 can be placed between the guide mechanism 3 and a target 4 of the bulk material. The guide mechanism 3 can be any of those known in the art including piezo-mirrors, acousto-optic deflectors, rotating polygons, a vibration mirror, or prisms. Preferably the guide mechanism 3 is a vibration minor 3 to enable controlled and rapid movement of the laser beam 1. The guide mechanism 3 directs the laser beam 1 to a target 4. In one embodiment, the target 4 is a bulk gold target. The target 4 is submerged a distance, from several millimeters to preferably less than 1 centimeter, below the surface of a suspension liquid 5. The target 4 is positioned in a container 7 additionally but not necessarily having a removable glass window 6 on its top. Optionally, an O-ring type seal 8 is placed between the glass window 6 and the top of the container 7 to prevent the liquid 5 from leaking out of the container 7. Additionally but not necessarily, the container 7 includes an inlet 12 and an outlet 14 so the liquid 5 can be passed over the target 4 and thus be re-circulated. The container 7 is optionally placed on a motion stage 9 that can produce translational motion of the container 7 with the target 4 and the liquid 5. Flow of the liquid 5 is used to carry the nanoparticles 10 generated from the target 4 out of the container 7 to be collected as a colloidal suspension. The flow of liquid 5 over the target 4 also cools the laser focal volume. The liquid 5 can be any liquid that is largely transparent to the wavelength of the laser beam 1, and that serves as a colloidal suspension medium for the target material 4.

In one embodiment, the liquid 5 is deionized water having a resistivity of greater than 0.05 MOhm·cm, and preferably greater than 1 MOhm·cm. The system thus allows for generation of colloidal gold nanoparticles in situ in a suspension liquid so that a colloidal gold suspension is formed.

The formed gold nanoparticles are immediately stably suspended in the liquid and thus no dispersants, stabilizer agents, surfactants or other materials are required to maintain the colloidal suspension in a stable state. This result was unexpected and allows the creating of a unique colloidal gold suspension that contains bare gold nanoparticles.

The following laser parameters were used to fabricate gold nanocolloids by pulsed laser ablation of a bulk gold target in deionized water: pulse energy of 10 uJ (micro Joules), pulse repetition rate of 100 kHz, pulse duration of 700 femtoseconds, and a laser spot size on the ablation target of about 50 um (microns). For the preparation of Au nanocolloids according to the present invention, a 16 mm (millimeter) long, 8 mm wide, and 0.5 mm thick rectangular target of Au from Alfa Aesar was used. For convenience, the Au target materials can be attached to a bigger piece of a bulk material such as a glass slide, another metal substrate, or a Si substrate.

More generally, for the present invention the laser ablation parameters are as follows: a pulse duration in a range from about 10 femtoseconds to about 500 picoseconds, preferably from about 100 femtoseconds to about 30 picoseconds; the pulse energy in the range from about 1 µJ to about 100 µJ; the pulse repetition rate in the range from about 10 kHz to about 10 MHz; and the laser spot size may be less than about 100 µm. The target material has a size in at least one dimension that is greater than a spot size of a laser spot at a surface of the target material.

Two samples of colloidal gold nanoparticles were characterized by an array of commercially available analytic instruments and techniques, including UV-VIS absorption spectra, dynamic light scattering (DLS), transmission electron microscopy (TEM), and Fourier transformed infrared spectroscopy (FTIR). One of the samples was a commercially available wet chemical produced citrate-capped colloidal gold preparation and the second sample was colloidal gold prepared according to the present invention. UV-VIS absorption spectra were recorded with a Shimadzu UV-3600 UV-VIS-NIR spectrophotometer. DLS measurements were performed using a Nano-ZS90 Zatasizer (Malvern Instrument, Westborough, Mass.). Infrared spectra were recorded on a PerkinElmer spectrum 100 FT-IR spectrometer equipped with an ATR-diamond. Gold nanoparticles were visualized using transmission electron microscopy (TEM; JEOL 2010F, Japan) at an accelerating voltage of 100 kV. All measurements and processes were carried out at room temperature, approximately 25° C.

Figure 2:
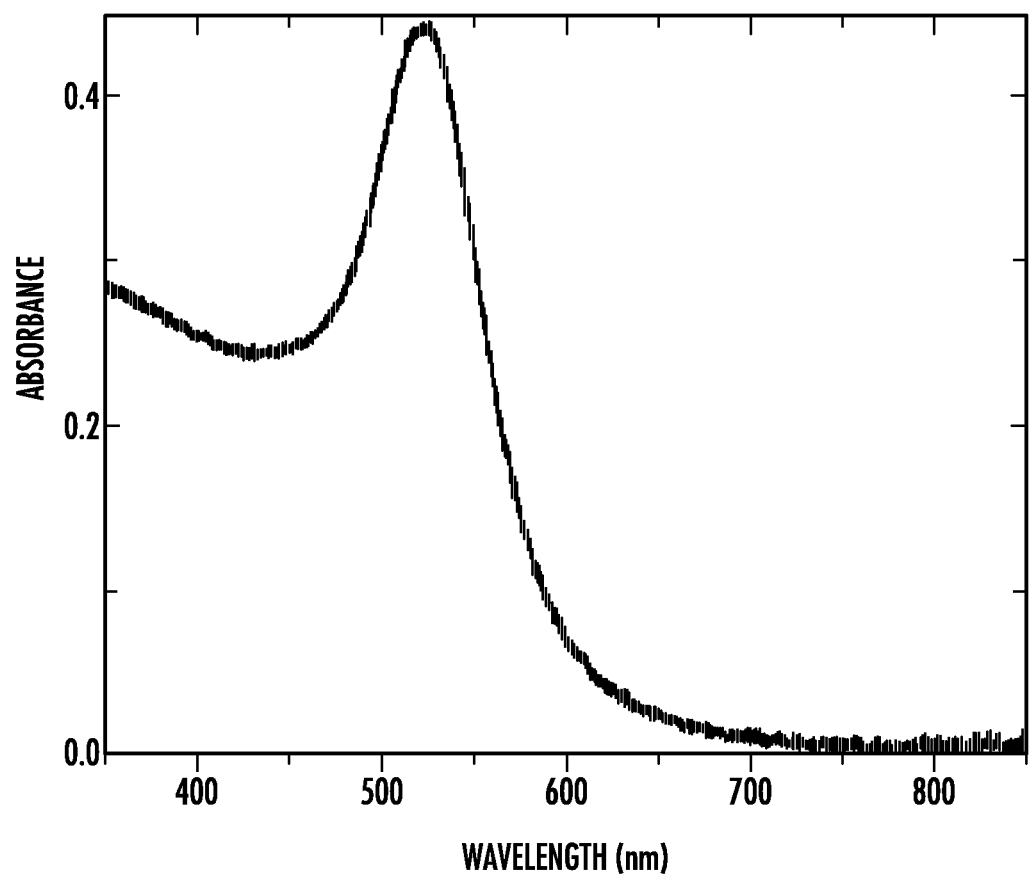
FIG. 2 displays the UV-VIS absorption spectrum of a commercially available citrate-capped gold nanoparticle preparation produced by a wet chemical approach, with an average particle diameter of 20 nanometers.

FIG. 2 displays the UV-VIS absorption spectrum of a commercially available spherical citrate-capped gold nanoparticle colloidal preparation, designated BBI Au nanocolloid, produced by a wet chemical approach with an average particle diameter of 20 nm. This sample was purchased from Ted Pella Inc., Redding, Calif. and was used without further purification. The maximum of the localized surface plasmon resonance of this Au nanocolloid is at 520 nm as can be seen.

Figure 3A:
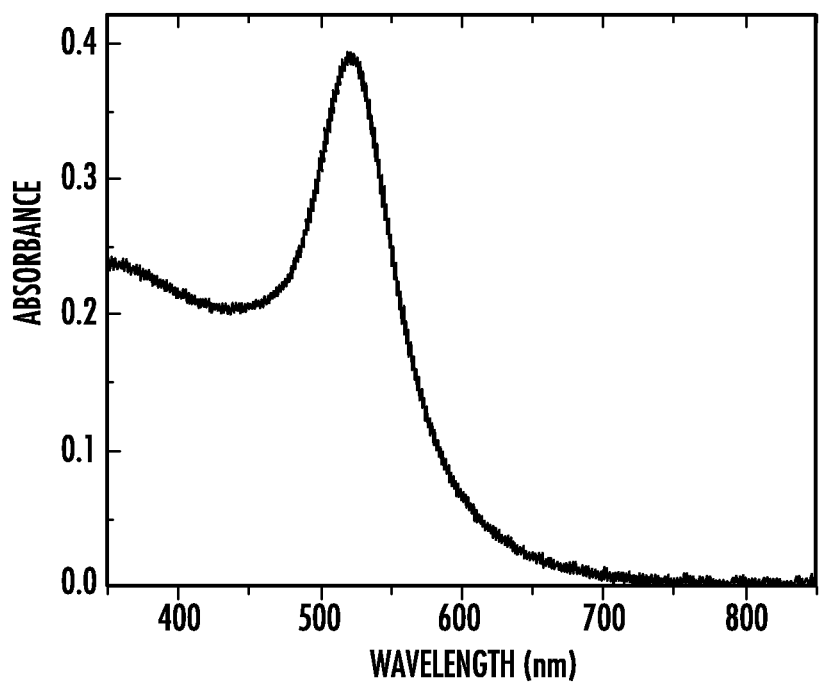
FIG. 3A illustrates the UV-VIS absorption spectrum of a stable bare colloidal gold preparation prepared according to the present invention by a laser ablation of a bulk gold target in deionized water.
Figure 3B:
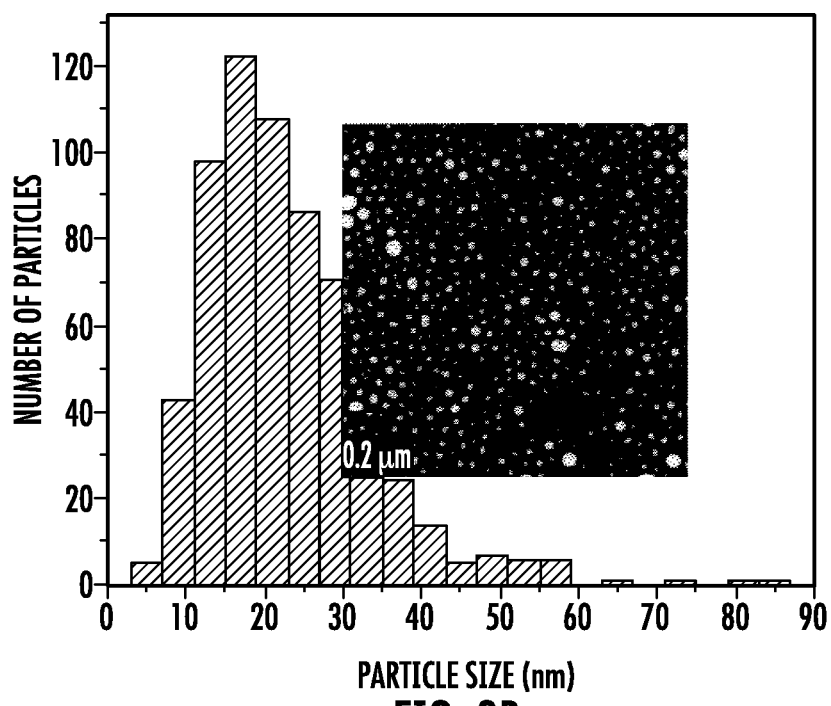
FIG. 3B shows in the inset a transmission electron microscopy (TEM) picture of the stable bare colloidal gold preparation and a histogram of the particle size distribution of the stable bare colloidal gold nanoparticles formed according to the present invention.

FIG. 3A shows the UV-VIS absorption spectrum of a stable bare colloidal gold nanoparticle preparation prepared by laser ablation in deionized water according to the present invention. The maximum of localized surface plasmon resonance of the colloidal gold nanoparticle preparation according to the present invention is the same as that of the BBI Au nanocolloid, which is at 520 nm. FIG. 3B shows a histogram of the Feret diameters of a sample of over 300 particles as measured from TEM images like the one shown in the inset. The average Feret diameter of the nanoparticles in the colloidal gold preparation of the present invention was determined to be 20.8 nm, which is very close to that of the BBI Au nanocolloid, by measurement of the core sizes of more than 300 nanoparticles from representative TEM images.

The shape, size, and optical properties of colloidal gold prepared according to the present invention are the same as those of the BBI Au nanocolloid. Therefore, the observed significant improvement in colloidal stability of gold nanoparticles generated by the present invention using pulse laser ablation followed by PEGylation as compared to that of gold nanoparticles prepared by a wet chemical approach, which will be shown in the following, should be not due to differences in size, shape, or optical properties.

Thiolated PEG (SH-PEG) with a molecular weight of 20 kiloDaltons (kDa), from Sigma Aldrich, product number 63753-250MG, was used without further purification. The PEGylation of gold nanoparticles was carried out by adding different amounts of the thiolated PEG into the colloidal gold samples. The final ratio between the number of thiolated PEG molecules with a molecular weight of 20 kDa and the number of Au nanoparticles in the mixed solution, determined by correlating their measured extinction (uv-vis) spectroscopy data to the extinction coefficient of 20 nm Au nanoparticles ($8\times10^8$ $mol^{-1}cm^{-1}$), was varied from 10 to 4000. After mixing, each solution was kept undisturbed for at least 24 hours at room temperature to provide a sufficient amount of time for PEG molecules to be conjugated onto the surfaces of the Au nanoparticles via Au-thiol bonding before characterizing the colloidal stability of the Au nanoparticles under PEGylation.

The colloidal stability of the two colloidal Au nanoparticle preparations under PEGylation was evaluated by measuring the UV-VIS absorption spectroscopy, which is considered to be the most appropriate technique due to the existence of intense localized surface plasmon resonance of Au nanoparticles around 520 nm, of the preparations. The aggregation and/or precipitation of gold nanoparticles under PEGylation will be reflected by a decrease of the absorption around 520 nm.

Figure 4A:
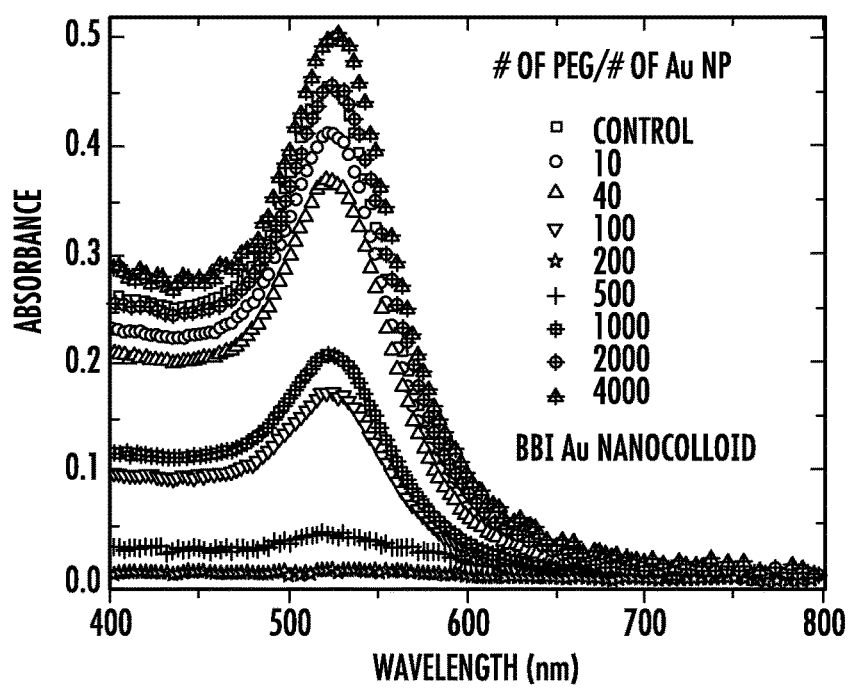
FIG. 4A displays the UV-VIS absorption spectra of commercially available colloidal gold nanoparticles mixed with various amounts of thiolated polyethyleneglycol (PEG), FIG. 4B displays the UV-VIS absorption spectra of colloidal gold prepared according to the present invention mixed with various amounts of thiolated PEG.
Figure 4B:
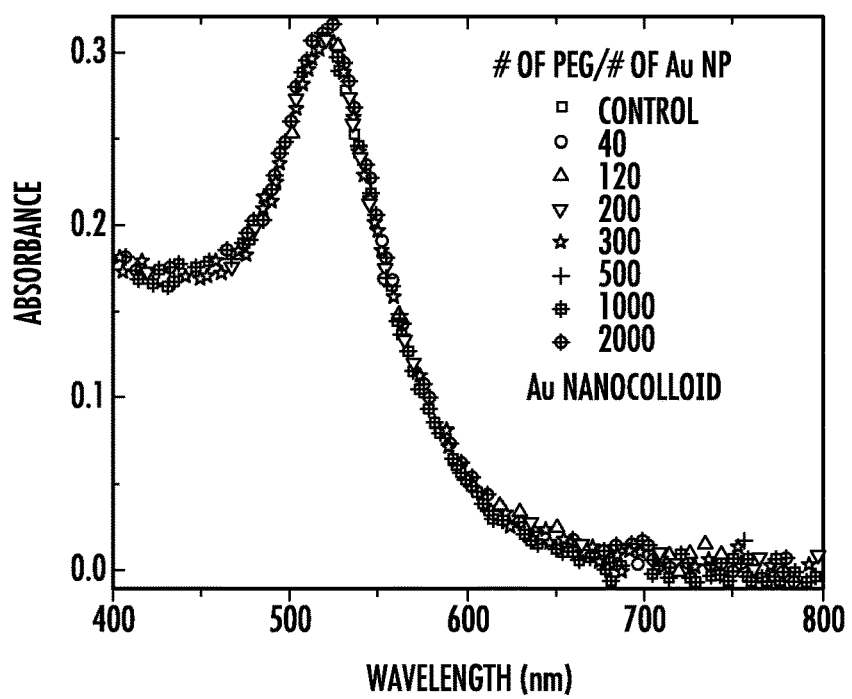

FIGS. 4A and 4B display the UV-VIS absorption spectra of the various gold nanocolloids after mixing with thiolated PEG at different concentrations and then letting them sit for at least 24 hours. FIG. 4A is for the samples using the wet chemical BBI Au nanocolloids and FIG. 4B is for the samples using the Au nanocolloids prepared according to the present invention. The differences between FIGS. 4A and 4B are very obvious. For the PEGylation of the BBI Au nanocolloids, the absorbance around 520 nm varies widely depending on the ratio between the number of PEG molecules and the number of Au nanoparticles, with the decrease from the control value of about 0.45 representing aggregation/precipitation of particles. In contrast to that of BBI Au nanocolloids, for the PEGylation of the Au nanocolloids prepared according to the present invention, the mixing with various amounts of thiolated PEG induced a negligible change in the spectrum as compared with that of the Au nanocolloid without adding PEG, which served as a control sample. All the spectra of PEGylated Au nanocolloids prepared according to the present invention are almost the same as that of the control sample. There are no detectable red shifts or decreases of localized surface plasmon resonance in all the spectra of these samples. The lack of any loss of the intensity around 520 nm reveals the superior colloidal stability of colloidal gold prepared according to the present invention during the PEGylation process.

Figure 5A:
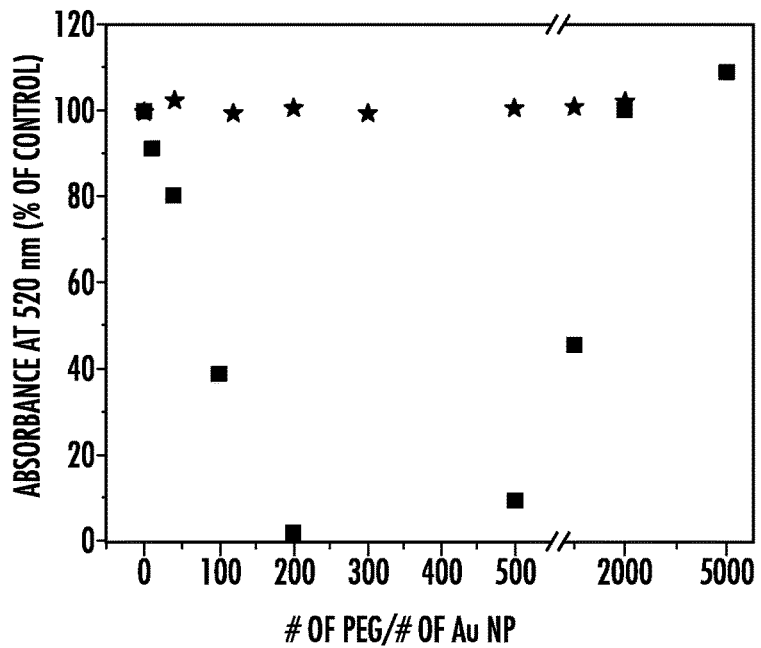
FIG. 5A shows the data from FIG. 4A and FIG. 4B in graphical form to demonstrate colloidal stability of the gold nanoparticles during surface functionalization with thiolated PEG characterized by monitoring the change of the absorbance of the localized surface plasmon resonance of gold nanocolloids at 520 nanometers, FIG. 5B schematically illustrates surface coverage ranging from 0% to 100% of thiolated PEG on the surface of gold nanoparticles prepared according to the present invention.

The experimental results displayed in the FIGS. 4A and 4B are summarized in FIG. 5A wherein the absorbance at 520 nm of the various samples is expressed as a percentage of the respective control sample with no PEGylation. The solid squares are for the BBI Au nanocolloid samples and the solid stars are for the Au nanocolloids prepared according to the present invention. The data for the BBI samples shows that the colloidal gold begins to precipitate as soon as you start adding the thiolated PEG and continues until at a ratio of 200 thiolated PEG per AU nanoparticle you have complete precipitation. From 500 to 2000 thiolated PEG per Au nanoparticle the amount of precipitation starts to decrease and eventually the absorbance returns to the level with no PEG. By way of contrast, for colloidal gold prepared according to the present invention the absorbance at 520 nm did not change significantly at any ratio of PEG molecules to Au molecules compared with that of the control sample. Thus, there was no precipitation of nanoparticles from the colloidal gold prepared according to the present invention during PEGylation. This shows another significant advantage provided by colloidal gold prepared by the process of the present invention compared to the previous wet chemical colloidal gold.

Since the underlying mechanisms of the ligand exchange reaction during PEGylation are very complicated, it is not clear why irreversible aggregation/precipitation occurred during the PEGylation of the BBI Au nanocolloid. A possible explanation could be that there is a time gap between the time when the original surfactants, the citrate ions, leave the nanoparticle surface and the time when the nanoparticles bind with the new surfactants, the thiolated PEG, during the ligand exchange reaction. If this time gap is inversely proportional to the concentration of the incoming new surfactants, then increasing the concentration of the incoming new surfactants will shorten this time gap, which would decrease the possibility that the nanoparticles would become aggregated. This could explain the observed recovery of colloidal stability of the BBI Au nanocolloids as the concentration of the thiolated PEG molecules was increased.

Figure 5B:
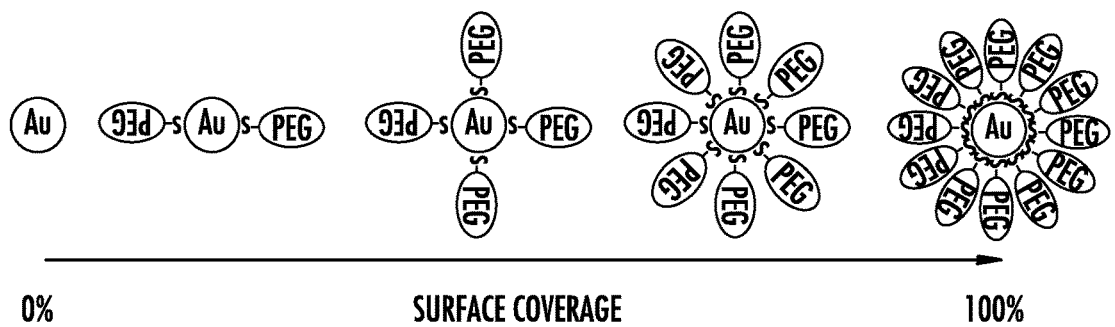

Since the colloidal stability is perfectly maintained during the PEGylation of colloidal gold prepared according to the present invention, this process allows one to prepare stable PEGylated Au nanocolloids having a defined number of conjugated PEG molecules on them ranging in amount from 1% or less to the number necessary for forming a complete monolayer on the surface of the gold nanoparticles. FIG. 5B schematically illustrates the surface coverage of thiolated PEG on the surface of gold nanoparticles ranging from 0% to 100%. The particle is idealized as a smooth sphere and every schematic drawing of PEG does not just represent a single PEG molecule but a group of PEG molecules.

Thiolated PEG molecules are used as an example for describing the conjugation of surface modifying molecules to the gold nanoparticles in the colloidal gold prepared according to the present invention. In fact, any functional ligand containing at least one functional group which exhibits affinity for gold surfaces, such as thiol groups, amine groups, or phosphine groups, could be conjugated to the surfaces of gold nanoparticles prepared using the method described above. This method allows one to produce stable gold nanocolloids with partial or full surface modification and thus the surface coverage of ligand on surfaces of gold nanoparticles can be tuned to be any percentage value between 0 and 100%.

Figure 6A:
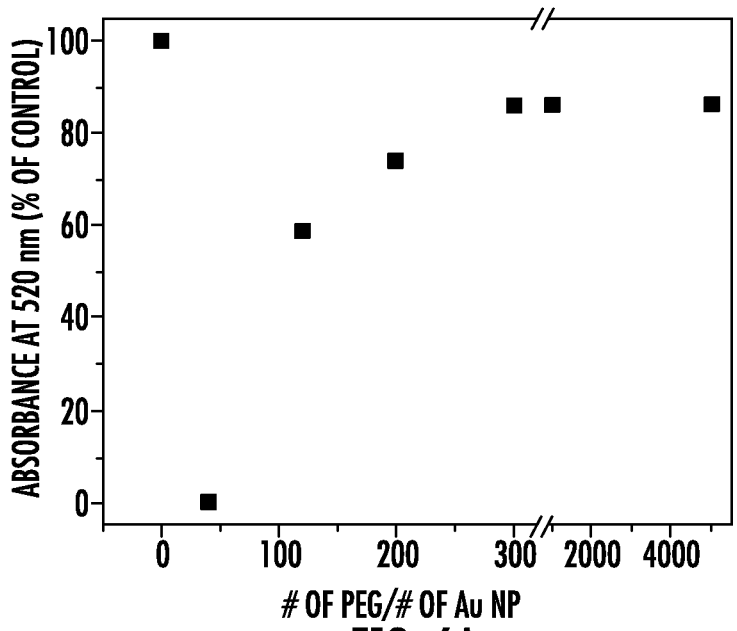
FIG. 6A displays the colloidal stability of PEGylated gold nanoparticles prepared in accordance with the present invention at various ratios of thiolated PEG to gold nanoparticles in the presence of 1% NaCl, characterized by absorbance of localized surface plasmon resonance of the gold nanoparticles at 520 nanometers.

The number of thiolated PEG 20 k molecules necessary to form a complete monolayer on the surface of colloidal gold nanoparticles prepared according to the present invention with average diameter of 20 nm can be determined. Due to the charge screening effect, as-synthesized gold nanocolloids prepared by both the present method and by the wet chemical approach will form aggregates at elevated salt concentrations. The layer of PEG molecules on the surface of gold nanoparticles can improve the stability of the gold nanoparticles in the presence of high levels of NaCl by providing a stearic repulsion between the nanoparticles and this stability approaches a maximum as the Au nanoparticle surface is completely coated with a layer of PEG molecules. Therefore, monitoring the stability of PEGylated colloidal gold nanoparticles prepared according to the present invention in the presence of NaCl can be used to determine the minimum amount of PEG molecules necessary to form a complete monolayer on the gold nanoparticle surface. Samples of colloidal gold nanoparticles prepared according to the present invention were PEGylated in the presence of ratios of thiolated PEG to Au nanoparticles of from 40 to 5000. NaCl was added to each sample to a final concentration of 1 weight percent (1%) to trigger aggregation/precipitation. FIG. 6A displays the absorbance of PEGylated Au nanocolloids at 520 nm expressed as a percentage of the control sample obtained without adding NaCl. It is shown that the stability of PEGylated Au nanoparticles initially drops, indicating aggregation, and then increases and approaches a maximum at a PEG/Au ratio of 300. Increasing the PEG/Au ratio beyond 300 to up to 5000 PEG per Au nanoparticle does not further increase stability of the colloidal suspension. This indicates that the minimum number of PEG molecules necessary for forming a complete monolayer on the surface of a bare gold nanoparticle with diameter of 20 nm prepared according to the present invention is between 200 and 300.

Figure 6B:
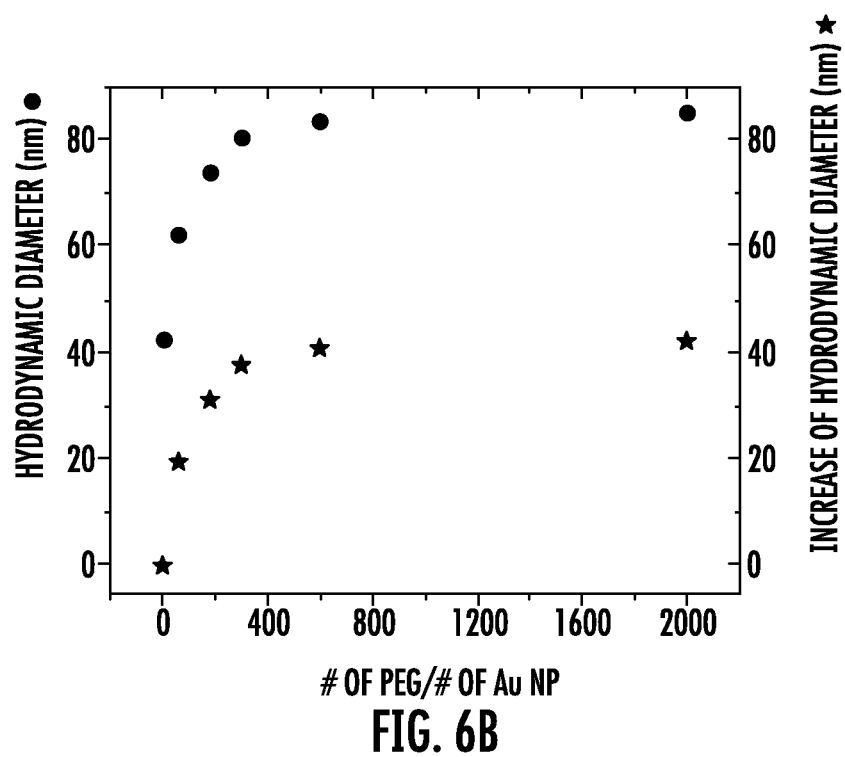
FIG. 6B illustrates the size increase measured by dynamic light scattering (DLS) of PEGylated gold nanoparticles prepared according to the present invention at various ratios of thiolated PEG to gold nanoparticles (NP)

Dynamic light scattering (DLS) was also used to verify the minimum number of thiolated PEG 20 kDa molecules necessary to form a complete monolayer on the surface of colloidal gold nanoparticles with an average diameter of 20 nm prepared according to the present invention by monitoring the size increase of the nanoparticles after PEGylation. Nanoparticles grow bigger as more PEG molecules are conjugated onto their surfaces. Use of DLS is considered by many to be a standard method for measuring the average nanoparticle size because of its wide availability, simplicity of sample preparation and measurement, relevant size range measurement from 1 nm to about 2 um, speed of measurement, and in situ measurement capability for fluid-born nanoparticles. FIG. 6B displays the results of both total size in the solid circles and the size increase in the solid stars of colloidal gold nanoparticles prepared according to the present invention that were PEGylated at the indicated ratios of thiol PEG to Au nanoparticles. It is shown that the total size and the increase in size approaches a maximum at a PEG/Au ratio of about 300 to 1 and that use of PEG at a level up to about 10 fold of this number had little additional effect on increasing the nanoparticle size. Again, the DLS measurement confirms that the minimum PEG molecule to Au ratio necessary for forming a complete monolayer on the surface of colloidal gold nanoparticles with an average diameter of 20 nm prepared according to the present invention is between 200 and 300. This result is consistent with the result of the stability test using 1% NaCl as reported in FIG. 6A.

Figure 7A:
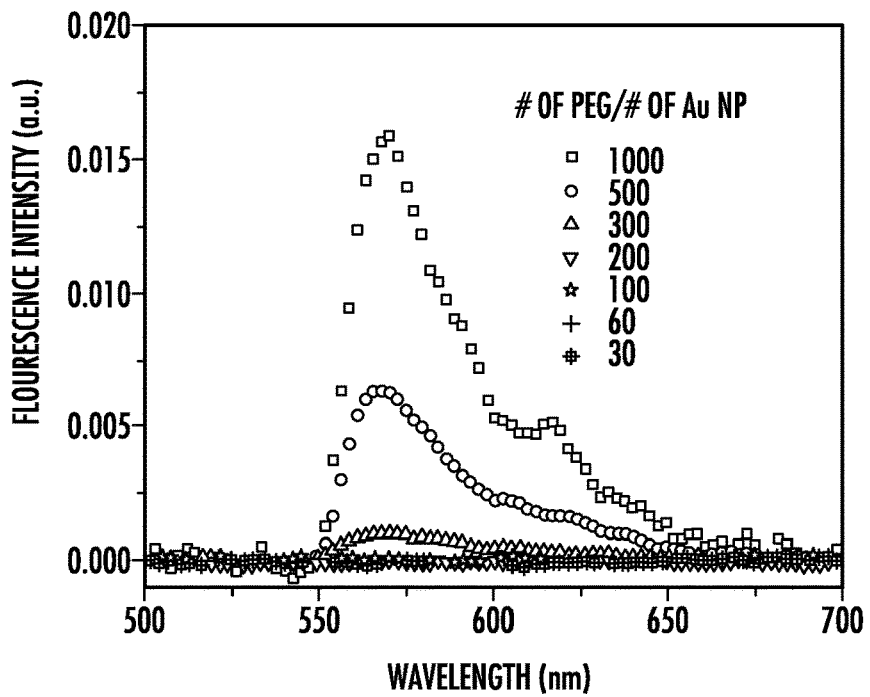
FIG. 7A displays the fluorescence spectra of various mixtures of Rhodamine labeled PEG with Au nanoparticles prepared according to the present invention and FIG. 7B illustrates the fluorescence intensity at 570 nm of these mixtures as a function of initial input ratio between the number of Rhodamine labeled PEG molecules and the number of Au nanoparticles in the mixed solution.
Figure 7B:
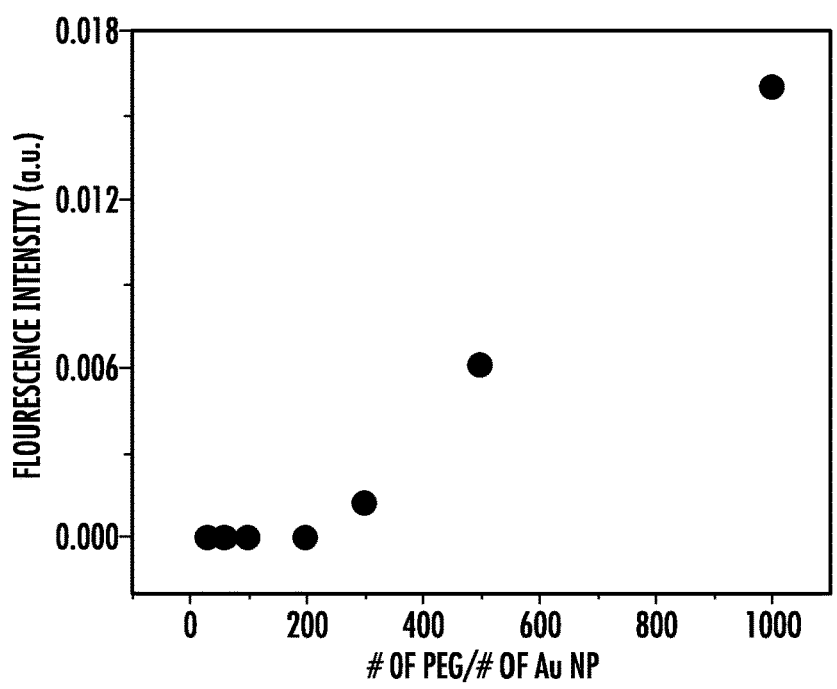

A third method was used to determine the minimum number of thiolated PEG molecules necessary to form a complete monolayer on the surface of colloidal gold nanoparticles prepared according to the present invention. Again the colloidal gold nanoparticles had an average diameter of 20 nm. In this measurement fluorescently tagged PEG molecules were used. The thiolated PEG was 10 kDa and it was tagged with Rhodamine. It is well known that gold nanoparticles quench almost all fluorescence from fluorescent molecules bound to their surfaces. Therefore it is expected that at low ratios of Rhodamine labeled PEG to Au nanoparticles there should be very little fluorescence as they will all be bound and therefore quenched. As the ratio of Rhodamine labeled PEG to Au nanoparticles increases it should reach a point where there are free Rhodamine labeled PEG since all the binding sites on the Au nanoparticles are occupied. At that ratio one should begin to detect fluorescence. In this measurement the Rhodamine labeled PEG was mixed with colloidal gold nanoparticles prepared according to the present invention at a series of ratios as shown in FIG. 7A. FIG. 7A displays the fluorescence spectrum from several solutions of gold nanoparticles conjugated with Rhodamine label thiolated PEG 10 k molecules. It is seen that fluorescence was only detected from the solution of gold nanoparticle-Rhodamine labeled PEG 10 k conjugates if the initial input PEG/Au ratio was above 300 PEG per Au nanoparticle. The result indicates that only as the PEG/Au ratio is above 300, are there free unbound PEG molecules in the solution. We did not observe any fluorescence when the PEG/Au ratio was 200, which indicates that all the Rhodamine labeled PEG 10 kDa molecules added to the gold nanocolloid were bound to the surfaces of nanoparticles. In FIG. 7B the intensity of the fluorescence peak at 570 nm for all the ratios is also plotted. Again this shows that no fluorescence is observed until the ratio is between 200 and 300 and thereafter it increases linearly. This again confirms that the minimum number of PEG molecules necessary for forming a complete monolayer on the surface of colloidal gold nanoparticles prepared according to the present invention with an diameter of 20 nm is between 200 and 300.

The footprint size of a thiol group on the surface of a gold nanoparticle has been determined by others using thiol-terminated oligonucleotides. Hill, H. D., Millstone, J. E., Banholzer, M. J., and Mirkin, C. A., *ACS Nano*, Vol. 3 (2009), 418-424. The footprint value depends on the diameter of the gold nanoparticles. For a nanoparticle size of 20 nm, it is 7.0 +/−1 $nm^2$. Therefore, for a spherical gold nanoparticle with a diameter of 20 nm, the minimum number of thiol-terminated molecules necessary to form a complete monolayer on the surface of the gold nanoparticle is about 180 +/−20 by referring to this literature value, which is fairly close to the results from the three other measures described above.

All three methods described above for determining the minimum number of thiol-terminated molecules necessary to form a complete monolayer on the surface of colloidal gold nanoparticles prepared according to the present invention are important. The same processes can be carried out for other ligands to determine their footprint sizes. Knowing this minimum number, one can create conjugation reactions wherein the amount of surface coverage is set at any level from 0 to 100% coverage thereby enabling tunable conjugation. One can add mixtures of ligands and be certain of the ratio that should appear on the final conjugated Au nanoparticle. In addition, one can add enough ligand to ensure complete coverage without having the previously required large excess of ligand. Therefore, the process becomes feasible for use with very rare or expensive ligands. Preferably the total amount of all ligands used during the ligand exchange reaction does not exceed the amount required to form a complete monolayer, as determined by any method including those described above, on the Au nanoparticles prepared according to the present invention by more than 200%, thereby providing no more than a 200% excess non-conjugated free ligand. For example if it is determined that an initial ligand to Au nanoparticle ratio of 300:1 provides a complete monolayer, then the total amount of all ligands used in a ligand exchange reaction would not exceed 900:1. Preferably, the amount of excess free ligand does not exceed 20% more than the amount required to form a monolayer on the particles. This permits tunable ligand coverage of from 0 to 100%, preferably 1% to 100%, and use of rare or expensive ligands. Obviously, the ratio initial ratio required will be a function of the size of the Au nanoparticles with larger particles requiring a higher initial ratio because of the larger surface area for coverage. Thus, the present specification also provides several methods for determining this area for Au nanoparticles.

Figure 8:
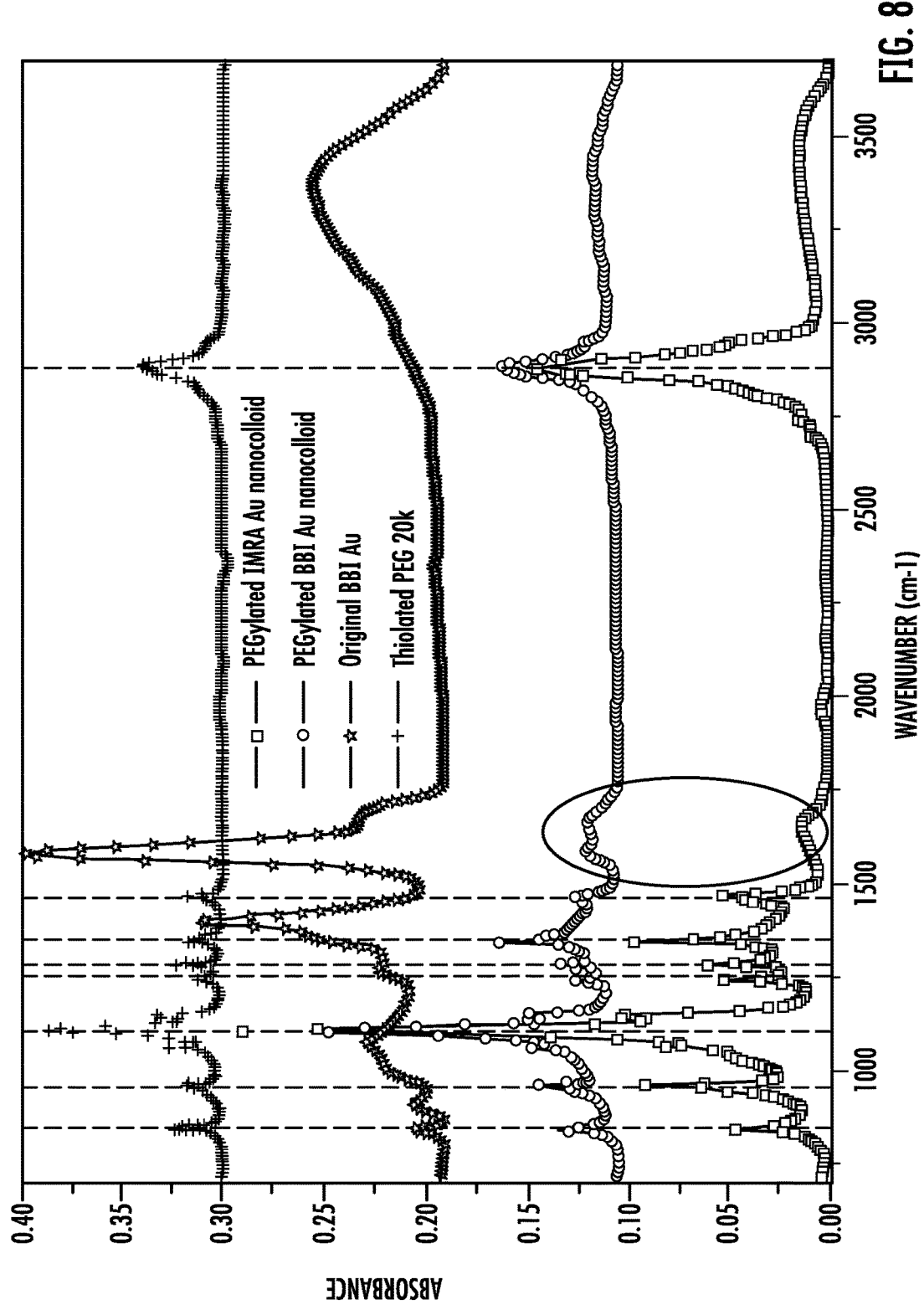
FIG. 8 displays the Fourier transform infrared spectroscopy (FTIR) spectra of the following from top trace to bottom trace the thiolated PEG 20 kDa, the original citrate-capped BBI Au nanocolloid solution, PEGylated BBI Au nanocolloid solution, PEGylated Au nanocolloid solution wherein the colloidal gold nanoparticles were prepared according to the present invention, the dashed lines indicate the characteristic peaks for thiolated PEG 20 kDa.

FTIR spectroscopy was also used to confirm the binding of thiolated PEG 20 kDa to the surface of colloidal gold nanoparticles. As displayed in the top trace in FIG. 8, the FTIR spectra of thiolated PEG 20 kDa shows a series of peaks and the dashed lines in the Figure show that these same peaks are found in the two PEGylated samples but not in the original citrate-capped BBI Au nanoparticles. The traces from the top down are the following: the thiolated PEG 20 kDa, the original citrate-capped BBI Au nanocolloid solution, PEGylated BBI Au nanocolloid solution, and PEGylated Au nanocolloid solution wherein the colloidal gold nanoparticles were prepared according to the present invention. In this experiment the ratio of PEG molecules to Au nanoparticles was 2000 to 1 for both PEGylation samples. As shown in the data in FIG. 5A this ratio is sufficient to ensure total coverage and maximal stability of the samples as measured by absorbance at 520 nm. The major difference between the FTIR spectrum of the PEGylated Au nanocolloid prepared according to the present invention and that of PEGylated BBI Au nanocolloid is within range from 1500 $cm^{-1}$ to 1750 $cm^{-1}$. In this range, PEGylated Au nanocolloid prepared according to the present invention shows just one peak at around 1661 $cm^{-1}$. The PEGylated BBI Au nanocolloid, however, shows two peaks with one at around 1661 $cm^{-1}$ and the other peak at around 1584 $cm^{-1}$, which is a characteristic peak of citrate. The same peak at around 1584 $cm^{-1}$ is seen at a much larger level in the spectra of the original citrate-capped BBI Au nanocolloid. This data indicates that the original citrate surfactant on the BBI Au nanoparticles could not be completely removed by a ligand exchange reaction driven to completion using thiolated PEG molecules. It also serves as a marker to identify non-citrate formed Au nanocolloids such as prepared according to the present invention which are bare pure Au nanocolloids with no surface bound ligands as prepared.

Figure 9:
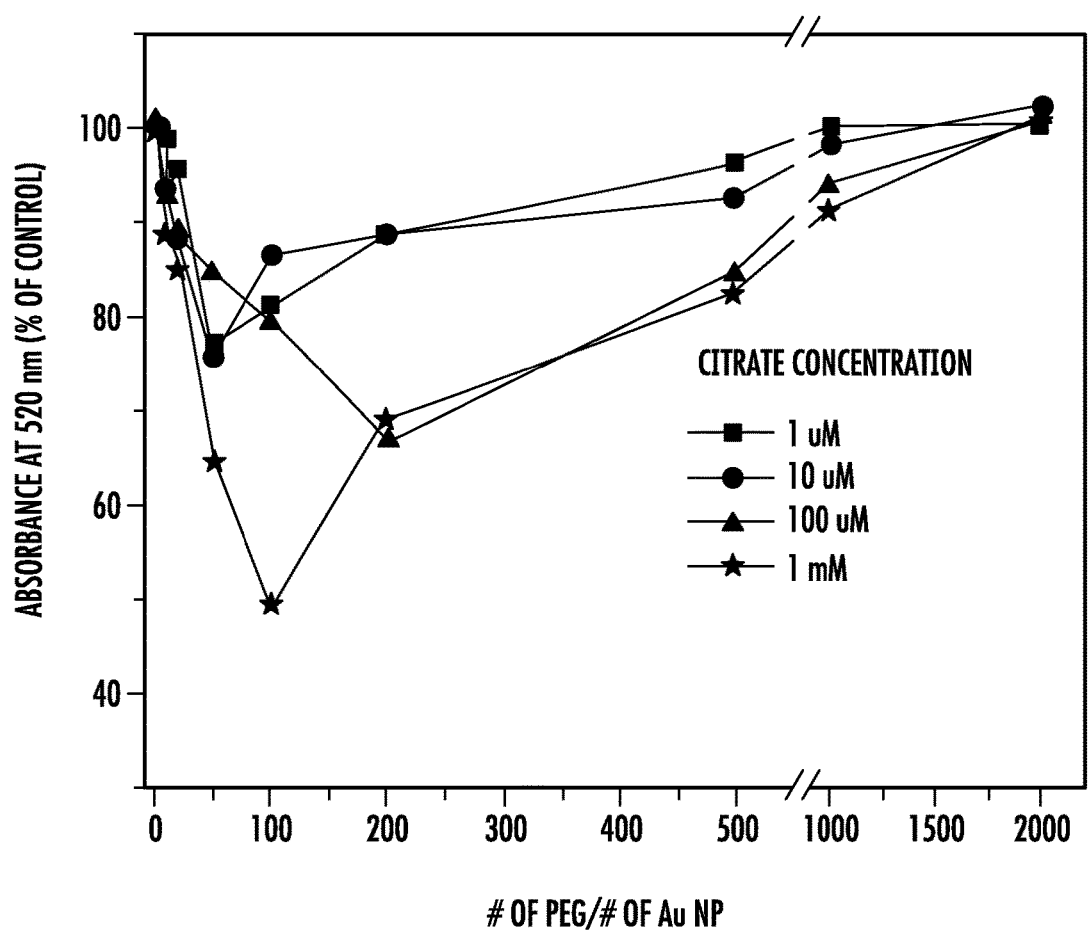
FIG. 9 displays the colloidal stability of colloidal gold nanoparticles prepared according to the present invention during surface modification with thiolated PEG in the presence of various amounts of citrate by monitoring the change of the absorbance of the localized surface plasmon resonance of gold nanocolloids at 520 nm.

The effect of citrate on the colloidal stability of colloidal gold nanoparticles prepared according to the present invention during a PEGylation reaction was also investigated. This was accomplished by monitoring the absorbance at 520 nm during the PEGylation reaction. As shown in FIGS. 4B and 5A there should be minimal changes to this absorbance if the surface of the Au nanoparticles are bare, which they are when prepared according to the present invention. Any significant decrease in absorbance would indicate that the Au nanoparticles are aggregating while a significant increase would indicate an increase in colloidal stability. In the data presented in FIG. 9 the PEGylation was carried out in the presence of citrate at the indicated levels ranging from 1 microMolar (µM) to 1 milliMolar (mM). As shown, all the tested levels of citrate caused a decrease in stability at low ratios of PEG to Au nanoparticles during the PEGylation. The stability was eventually restored as the ratio of PEG to Au was increased even at the highest level of citrate. This demonstrates that thiol group-based conjugation could be used to characterize the surface chemistry of colloidal gold nanoparticles and/or to detect the presence of chemical additives or impurity in the colloidal solution by varying the concentration of thiol-containing ligand and measuring the change of the UV-VIS absorption spectrum. The data was generated using thiolated PEG, but other thiolated ligands are expected to show similar results although the spectrum may have an absorbance peak at a different location in the spectra.

Because the present invention allows one to prepare bare stable colloidal gold nanoparticles and since one can measure the surface area thereby determining the amount of a first ligand required for any coverage of from 0 to 100%, the colloidal gold nanoparticles prepared according to the present invention can be used to conjugate a second type of ligand with a different functionality from the first to the same nanoparticle. Therefore, stable colloidal gold nanoparticles conjugated with two or more different ligands with different functionalities could be fabricated by employing this protocol.

In the data described in this specification, thiolated PEG 20 kDa molecules or thiolated Rhodamine labeled PEG 10 kDa molecules were used, these were chosen for illustration purposes only. The invention is not limited to use with thiolated PEG molecules. Because the invention produces bare stable colloidal gold nanoparticles, any ligand having a group that can bind to Au particle surfaces can be used such as the suggested thiol, amine, or phosphine groups. In addition, since the Au nanoparticles are bare even ligands not normally used, i.e. those with low affinity for Au surfaces can be used. This is because the present invention allows for direct ligand binding without the need for an "exchange" to occur. There is not a need to have a competitive reaction between stabilizer molecules and the desired ligand, the entire gold surface is free and available for binding to a ligand. This also makes colloidal gold nanoparticles prepared according to the present invention very attractive for use in binding aptamers and other rare or expensive ligands. The aptamers can be deoxyribonucleic acid (DNA) or ribonucleic acid (RNA) or amino acid sequences as is known in the art. The present colloidal gold can also be used to bind to antibodies, enzymes, proteins, peptides and other reporter or ligand materials that are rare or expensive. The ligands can include any fluorescent marker having a group or bound to a group that can be conjugated to a Au nanoparticle. This does not exclude exchange reactions, but unlike wet chemical produced colloidal gold it is not a necessary reaction. In addition, all kinds of PEG molecules, comprising mono-, homo-, and heterofunctional PEG with different functional groups and one or multiple arms and molecular weights ranging from 200 Da to 100,000,000 Da can also be used for the surface modification reaction. In the case of using heterofunctional PEG, the functional groups, for example a carboxyl group COOH and an amine group $NH_2$, not used to bind to the Au nanoparticle could be used for binding to other functional groups on other ligands. This opens a wide range of possibilities for other functionalities to be added to the Au nanoparticles.

Compared with PEGylated colloidal gold nanoparticles prepared by wet chemical processes, the PEGylation of Au gold nanoparticles fabricated by the present top-down nanofabrication method will form gold nanoparticle conjugates with improved biocompatibility because of the high efficiency and excellent stability of the PEGylation processes using the nanoparticles prepared according to the present invention. Therefore, they are expected to have a longer systemic blood circulation time which ensures that more of these nanoparticles will be delivered to the target sites of interest for imaging, diagnosis, drug delivery, and photoresponsive therapy of diseases.

In the present specification the concentration has been on colloidal Au nanoparticles, however, since the PEGylation process can be used for many other metals it is expected that the present top-down fabrication method can also be applied to other metals which can then be partially or fully surface modified using the processes described herein. For example, the metals and materials can be chosen from, but not limited to, Cr, Mn, Fe, Co, Ni, Pt, Pd, Ag, Cu, Silicon, CdTe, and CdSe.

The surface modification described herein is not limited to application to only spherical colloidal Au nanoparticles having a diameter of from 1 to 200 nanometers. In principle, this method should also work for colloidal Au nanoparticles with other shapes and configurations, including rods, prisms, disks, cubes, core-shell structures, cages, and frames, wherein they have at least one dimension in the range of from 1 to 200 nm. In addition, the method of surface modification described in this invention should also work for nanostructures which have outer surfaces that are only partially covered with gold.

Although the described process of top-down fabrication and surface modification was illustrated in embodiments wherein the liquid was deionized water it is possible to carry out the processes described in other liquids. For example, PEGylation surface modification can be carried out in water, methanol, ethanol, acetone, and other organic solvents. Likewise the step of formation of the colloidal nanoparticles can occur in these same liquids and others.

Examples of polymers other then PEG that can be used include polyacrylamide, polydecylmethacrylate, polymethacrylate, polystyrene, dendrimer molecules, polycaprolactone (PCL), polylactic acid (PLA), poly(lactic-co-glycolic acid) (PLGA), polyglycolic acid (PGA), and polyhydroxybutyrate (PHB).

In at least one embodiment, the colloidal gold nanoparticles are produced by laser ablation of a bulk gold target in deionized water followed by PEGylation and the PEGylated product is characterized by FTIR spectroscopy wherein the product exhibits a single detectable peak in the range between 1500 cm−1 and 1750 cm−1.

Thus, while only certain embodiments have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the embodiments described therein.

It is intended that the invention be limited only by the claims which follow, and not by the specific embodiments and their variations and combinations as described hereinabove.

What is claimed is:

1. A solution of colloidal gold nanoparticles comprising:
   said colloidal gold nanoparticles having been surface modified, wherein said surface modifications consist only of one or more ligands comprising a polyethylene glycol polymer with at least one thiol functional group, said at least one thiol functional group conjugating said one or more ligands to said gold nanoparticles, and wherein said gold nanoparticles are stable and dispersed in said solution;

wherein each of said one or more ligands is conjugated to said gold nanoparticles in an amount comprising surface coverage in the range of from 1 to 100% of a complete monolayer coverage of said one or more ligands on said gold nanoparticles; and wherein over the entire range of surface coverage said solution of colloidal gold nanoparticles has an absorbance peak at 520 nm +/− 2 nm and a localized surface plasmon resonance intensity of +/− 5% or less of an intensity of said solution of colloidal gold nanoparticles in an absence of said one or more ligands.

2. A solution of colloidal gold nanoparticles as recited in claim 1 wherein said amount of said one or more ligands conjugated to said gold nanoparticles comprises surface coverage in the range of from 1 to 80% of a complete monolayer coverage of said one or more ligands on said gold nanoparticles.

3. A solution of colloidal gold nanoparticles as recited in claim 1 wherein said amount of said one or more ligands conjugated to said gold nanoparticles comprises surface coverage in the range of from 1 to 60% of a complete monolayer coverage of said one or more ligands on said gold nanoparticles.

4. A solution of colloidal gold nanoparticles as recited in claim 1 wherein said amount of said one or more ligands conjugated to said gold nanoparticles comprises surface coverage in the range of from 1 to 40% of a complete monolayer coverage of said one or more ligands on said gold nanoparticles.

5. A solution of colloidal gold nanoparticles as recited in claim 1 wherein said amount of said one or more ligands conjugated to said gold nanoparticles comprises surface coverage in the range of from 1 to 20% of a complete monolayer coverage of said one or more ligands on said gold nanoparticles.

6. A solution of colloidal gold nanoparticles comprising:
said colloidal gold nanoparticles having surface modifications, said surface modifications consisting only of one or more ligands having one or more functional groups that bind directly to said gold nanoparticles and wherein said functional groups are selected from the group consisting of thiol groups, phosphine groups, amine groups and mixtures thereof;
wherein a surface coverage of said gold nanoparticles by said surface modifications consists of from 1% to 100% of a monolayer of coverage by said one or more ligands having one or more functional groups that bind directly to said gold nanoparticles, said 100% of a monolayer of coverage by said one or more ligands having been pre-determined by a footprint analysis of said one or more ligands bound to said gold nanoparticles; and
wherein said gold nanoparticles having surface modifications are stable and dispersed in said solution and wherein over the entire range of surface coverage said solution of colloidal gold nanoparticles has an absorbance peak at 520 nm +/− 2 nm and a localized surface plasmon resonance intensity of +/− 5% or less of an intensity of said solution of colloidal gold nanoparticles in an absence of said one or more ligands.

7. The solution of colloidal gold nanoparticles as recited in claim 1 wherein said ligand comprises a thiolated polyethylene glycol having a molecular weight in the range from 200 Daltons to 100,000,000 Daltons.

8. The solution of colloidal gold nanoparticles as recited in claim 1, wherein said ligand comprises at least one of a mono-, homo-, or a heterofunctional thiolated polyethylene glycol polymer with different functional groups and one or more arms.

9. The solution of colloidal gold nanoparticles as recited in claim 1, wherein said solution comprises gold nanoparticles surface modified with one or more thiolated polyethylene glycol ligands and exhibits a single detectable peak in the range between 1500 cm−1 and 1750 cm−1 as characterized by FTIR spectroscopy.

10. The solution of colloidal gold nanoparticles as recited in claim 6 wherein said solution comprises an amount of said one or more ligands which are not bound to said gold nanoparticles, said amount not bound being equal to or less than an amount of said one or more ligands equivalent to twice said amount necessary for 100% of a monolayer coverage on said gold nanoparticles in said solution based on said pre-determined footprint analysis of said one or more ligands bound to said gold nanoparticles.

11. The solution of claim 6, wherein said solution of colloidal gold nanoparticles is stable at room temperature of 25° C. for at least 24 hours with a detectable red shift of localized surface plasmon resonance and a decrease of localized surface plasmon resonance intensity induced by aggregation and/or precipitation of said gold nanoparticles being less than 2 nanometers and less than 10%, respectively.

12. The solution of claim 6, wherein said gold nanoparticles have at least one dimension in the range from about 1 nm to about 200 nm.

13. The solution of claim 6, wherein the shape of said gold nanoparticles comprises at least one of a sphere, a rod, a prism, a disk, a cube, a core-shell structure, a cage, a frame, or a mixture thereof.

14. The solution of claim 6, wherein said solution comprises at least one of water, methanol, ethanol, acetone, or another organic solvent.

15. The solution of claim 6, wherein said ligand comprises at least one of a polymer, a deoxyribonucleic acid nucleic acid sequence, a ribonucleic acid sequence, an aptamer, an amino acid sequence, a protein, a peptide, an enzyme, an antibody, a fluorescent marker, or a mixture thereof.

16. The solution of claim 6, wherein said ligand comprises a thiolated polyethylene glycol having a molecular weight in the range from 200Daltons to 100,000,000 Daltons.

17. The solution of claim 6, wherein said ligand comprises at least one of a mono-, homo-, or a heterofunctional PEG with different functional groups and one or more arms.

18. The solution of claim 6, wherein said solution comprises gold nanoparticles surface modified with PEG ligands and exhibits a single detectable peak in the range between 1500 cm−1 and 1750 cm−1 as characterized by FTIR spectroscopy.

19. The solution of claim 6, comprising gold nanoparticles which are surface modified with two or more different ligands in an amount comprising surface coverage in the range of from 1 to 100% of a monolayer coverage of said ligands on said gold nanoparticles.

20. The solution of colloidal gold nanoparticles as recited in claim 10 wherein, said gold nanoparticles are surface modified with said one or more ligands in an amount comprising surface coverage in the range of from 1% to 80% of a complete monolayer coverage of said ligands on said gold nanoparticles.

21. The solution of gold nanoparticles as recited in claim 10 wherein said gold nanoparticles are surface modified with said one or more ligands in an amount comprising surface coverage in the range of from 1% to 60% of a complete monolayer coverage of said ligands on said gold nanoparticles.

22. The solution of colloidal gold nanoparticles as recited in claim 10 wherein said gold nanoparticles are surface modified with said one or more ligands in an amount comprising surface coverage in the range of from 1% to 40% of a complete monolayer coverage of said one or more ligands on said gold nanoparticles.

23. The solution of colloidal gold nanoparticles as recited in claim 10 wherein said gold nanoparticles are surface modified with said one or more ligands in an amount comprising surface coverage in the range of from 1% to 20% of a complete monolayer coverage of said one or more ligands on said gold nanoparticles.

24. The solution of colloidal gold nanoparticles as recited in claim 19 comprising gold nanoparticles which are surface modified with two or more different ligands in an amount comprising surface coverage in the range of from 1 to 80% of a complete monolayer coverage of said two or more different ligands on said gold nanoparticles.

25. The solution of colloidal gold nanoparticles as recited in claim 19 comprising gold nanoparticles which are surface modified with two or more different ligands in an amount comprising surface coverage in the range of from 1 to 60% of a complete monolayer coverage of said two or more different ligands on said gold nanoparticles.

26. The solution of colloidal gold nanoparticles as recited in claim 19 comprising gold nanoparticles which are surface modified with two or more different ligands in an amount comprising surface coverage in the range of from 1 to 40% of a complete monolayer coverage of said two or more different ligands on said gold nanoparticles.

27. The solution of colloidal gold nanoparticles as recited in claim 19 comprising gold nanoparticles which are surface modified with two or more different ligands in an amount comprising surface coverage in the range of from 1 to 20% of a complete monolayer coverage of said two or more ligands on said gold nanoparticles.

* * * * *